(12) United States Patent
Sun et al.

(10) Patent No.: US 6,743,391 B2
(45) Date of Patent: Jun. 1, 2004

(54) SUPERABSORBENT POLYMERS HAVING DELAYED WATER ABSORPTION CHARACTERISTICS

(75) Inventors: Fang Sun, Lisle, IL (US); Bernfried A. Messner, Greensboro, NC (US); Heather S. Jones, Hixson, TN (US)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 10/301,928

(22) Filed: Nov. 21, 2002

(65) Prior Publication Data

US 2003/0118820 A1 Jun. 26, 2003

Related U.S. Application Data

(62) Division of application No. 09/602,852, filed on Jun. 26, 2000, now Pat. No. 6,514,615.
(60) Provisional application No. 60/141,412, filed on Jun. 29, 1999.

(51) Int. Cl.[7] ............................................. B29C 35/02
(52) U.S. Cl. ........................................ 264/345; 264/129
(58) Field of Search ................................. 264/345, 129, 264/131

(56) References Cited

U.S. PATENT DOCUMENTS

| 5,399,591 | A | * | 3/1995 | Smith et al. ................... 521/53 |
| 5,409,771 | A | * | 4/1995 | Dahmen et al. ............. 428/327 |
| 5,453,323 | A | * | 9/1995 | Chambers et al. ........... 428/402 |
| 6,239,230 | B1 | * | 5/2001 | Eckert et al. ............. 525/329.9 |
| 6,323,252 | B1 | * | 11/2001 | Gartner et al. .............. 521/149 |

* cited by examiner

Primary Examiner—Mary Lynn Theisen
(74) Attorney, Agent, or Firm—Smith Moore LLP

(57) ABSTRACT

A superabsorbent polymer comprising a delayed absorption superabsorbent polymer having a free water absorbency property of absorbing less than about 3 grams of aqueous saline per gram of superabsorbent polymer in about 6 seconds, for a full particle size distribution of superabsorbent polymer ranging from about 40 micrometers to about 890 micrometers.

9 Claims, No Drawings

SUPERABSORBENT POLYMERS HAVING DELAYED WATER ABSORPTION CHARACTERISTICS

This is a Divisional Application that claims priority to U.S. application Ser. No. 09/602,852 filed Jun. 26, 2000 now U.S. Pat. No. 6,514,615 and Provisional Application Serial No. 60/141,412 filed Jun. 29, 1999.

TECHNICAL FIELD

The present invention relates, in general, to absorbent polymers that absorb aqueous liquids (such as water, blood, and urine). More particularly, the present invention relates to superabsorbent polymers, namely polymers that absorb over 100 times their weight in water, which superabsorbent polymers have unique characteristics of delayed water absorption, and a novel method for making such superabsorbent polymers. As is well known, superabsorbent polymers have many uses, particularly in absorbent sanitary articles, such as disposable diapers, disposable adult incontinence garments, disposable sanitary napkins, and disposable bandages. The superabsorbent polymers of the present invention, due to their delayed water absorption characteristics, are particularly useful in the manufacture of a web of superabsorbent polymer and cellulosic fiber for use as a core composite in such sanitary articles, when the web is made by the wet-laid process.

DEFINITIONS OF ABBREVIATIONS

The following abbreviations are employed throughout this specification.

| Abbreviation | Definition |
| --- | --- |
| AUL | absorbency under load |
| All-PEGMA | allyloxy polyethylene glycol methacrylate, a X-linking agent |
| cm | centimeter |
| CRC | centrifuge retention capacity |
| X-linking | cross-linking |
| EO-TMPTA | ethoxylated trimethylol-propane triacrylate, a X-linking agent |
| FWA | free water absorption |
| mg | milligram |
| mm | millimeter |
| ppm | parts per million |
| psi | pounds per square inch |
| SAP | superabsorbent polymer, a polymer that absorbs over 50 times, more preferably over 75 times, even more preferably over 100 times, its weight in water |
| ABAH | 2,2'-azobis(2-amidino-propane) dihydrochloride, a polymerization initiator |

BACKGROUND OF THE INVENTION

When superabsorbent technology was first developed, only a high swelling capacity on contact of the superabsorbent polymer with liquids, referred to as the free swelling capacity in accordance with the free water absorption test (FWA), was the primary consideration. However, it was later realized that the water-absorbing polymers when present in a sanitary article, such as a diaper or incontinence garment, are subjected to mechanical load caused by movements of the person wearing the article. Thus, a new consideration arose in that the superabsorbent polymer, in addition to having a high swelling capacity, should also have a high capability for retaining liquid in accordance with the centrifuge retention capacity test (CRC) and a high absorbency under pressure in accordance with the absorbency under load test (AUL). A good discussion of the test for AUL can be seen in published European Patent Application No. 0 339 461 A1 (published Nov. 2, 1989; priority to U.S. Ser. Nos. 184,302 (Parent) and 334,260 (Continuation-in-Part), which Continuation-in-Part has issued as U.S. Pat. No. 5,147,343) to Kellenberger, assignor to Kimberly-Clark Corporation.

Published European Patent Application No. 0 437 816 A1 (published Jul. 24, 1991; priority to U.S. Ser. No. 464,798) to Kim and Nielsen, assignors to Hoechst Celanese Corporation, shows the wet-laid process for the manufacture of webs of superabsorbent polymer and cellulosic fiber. These webs are employed as core composites in disposable sanitary articles, such as those mentioned above. More particularly, disclosed is a process that involves blending superabsorbent polymer particulates with a liquid to form a slurry, followed by mixing cellulosic fibers with the slurry and then filtering to remove part of the liquid, and finally drying the resultant. The wet-laid process is also described in U.S. Pat. No. 4,605,401 (issued Aug. 12, 1986) to Chmelir and Künschner, assignors to Chemische Fabrik Stockhausen GmbH.

The journal article, "Keeping Dry with Superabsorbent Polymers", Chemtech, (September, 1994) by Buchholz, contains an excellent discussion of the conventional methods for making superabsorbent polymers, certain of which have sulfonate functional groups and certain of which have carboxylic acid functional groups. Also, Buchholz discussed various uses for superabsorbent polymers, such as in the above-noted sanitary articles, as well as in a sealing composite between concrete blocks that make up the wall of underwater tunnels and in tapes for water blocking in fiber optic cables and power transmission cables.

A good discussion of the methods for making superabsorbent polymers can also be seen in U.S. Pat. No. 5,409,771 (issued Apr. 25, 1995) to Dahmen and Mertens, assignors to Chemische Fabrik Stockhausen GmbH. More specifically, this patent mentions that commercially available superabsorbent polymers are generally cross-linked polyacrylic acids or cross-linked starch-acrylic-acid-graft-polymers, the carboxyl groups of which are partially neutralized with sodium hydroxide or caustic potash. Also mentioned is that the superabsorbent polymers are made by two methods, one being the solvent polymerization method and the other being the inverse suspension or emulsion polymerization method.

In the solvent polymerization method, an aqueous solution of partially neutralized acrylic acid for instance and a multi-functional network cross-linking agent is converted to a gel by radical polymerization. The resultant is dried, ground, and screened to the desired particulate size.

On the other hand, in the inverse suspension or emulsion polymerization method, an aqueous solution of partially neutralized acrylic acid for instance is dispersed in a hydrophobic organic solvent by employing colloids or emulsifiers. Then, the polymerization is started by radical initiators. Water is azeotropically removed from the reaction mixture after completion of the polymerization, followed by filtering and drying the resultant product. Network cross-linking typically is accomplished by dissolving a polyfunctional cross-linking agent in the monomer solution.

Furthermore, U.S. Pat. No. 5,154,713 (issued Oct. 13, 1992) to Lind and U.S. Pat. No. 5,399,591 (issued Mar. 21, 1995) to Smith and Lind, both of which patents are assigned to Nalco Chemical Company, describe new processes for making superabsorbent polymers, as a result of which the superabsorbent polymers display an increased, faster water absorption. The superabsorbent polymers are depicted as useful as absorbents for water and/or for aqueous body fluids when the polymers are incorporated into absorbent structures, such as disposable diapers, adult incontinence garments, and sanitary napkins.

General background with respect to various superabsorbent polymers and methods of manufacturing them can be seen in U.S. Pat. No. 5,229,466 (issued Jul. 20, 1993) to Brehm and Mertens; U.S. Pat. No. 5,408,019 (issued Apr. 18, 1995) to Mertens, Dahmen, and Brehm; and U.S. Pat. No. 5,610,220 (issued Mar. 11, 1997) to Klimmek and Brehm, all of which patents are assigned to Chemische Fabrik Stockhausen GmbH.

The disclosures of all above-mentioned patents and published patent applications are incorporated herein by reference.

BRIEF SUMMARY AND OBJECTS OF THE INVENTION

Accordingly, the present invention provides a delayed absorption, particulate superabsorbent polymer comprising polymeric particles having a free water absorption property of absorbing less than about 3 grams of water per gram of polymeric particle in about 6 seconds, for a full particle size distribution from about 40 to about 890 micrometers.

Also, the present invention provides a method for making such superabsorbent polymers having the free water absorption property described in the paragraph above, wherein the method comprises a first step of preparing a particulate superabsorbent polymer by conventional methods, followed by a second step of subjecting the resultant particulate polymeric particles to a two-part thermal profile. Preferably, the two-part thermal profile comprises (a) heating the polymeric particles for about 30 to about 90 minutes at a temperature that increases during the heating from a beginning temperature between about 50 and about 80° C. to a final temperature between about 170 and about 220° C., followed by (b) maintaining the resultant, heated polymeric particles from (a) for about 30 to about 90 minutes at a constant temperature between about 5 and about 50° C. higher than the final temperature of (a).

Additionally, the present invention provides a wet-laid web comprising a fibrous component and a component of the delayed absorption superabsorbent polymers described in the two paragraphs above. Furthermore, the present invention provides a method for improving the solids content of a wet-laid web by making the web with the delayed absorption superabsorbent polymers described in the two paragraphs above.

Therefore, it is an object of the present invention to provide a superabsorbent polymer having a decreased, slower free water absorption as compared to prior art superabsorbent polymers of similar particulate size, which typically have a free water absorption of more than 5 grams of water per gram of polymeric particles at 6 seconds, often more than 7 grams of water per gram of polymeric particles at 6 seconds, and in certain instances, more than 20 grams of water per gram of polymeric particles at 6 seconds.

Furthermore, it is an advantage of the present delayed absorption, superabsorbent polymers that they have not only an acceptable absorbency under load but also an improved solids content, as a result of which they are very useful in a wet-laid web of superabsorbent polymer and cellulosic fiber for use as a core composite in sanitary articles.

Moreover, it is another advantage that due to the decreased free water absorption property of the present superabsorbent polymers, they are particularly useful in making a web by the wet-laid process since the decreased free water absorption should lead to less water uptake during the wet-laid process of blending an aqueous slurry of superabsorbent polymer and cellulosic fiber, which in turn, should lead to less drying time of the resultant web prior to placing it as a core composite in the end product, such as a disposable diaper, a disposable adult incontinence garment, or a disposable sanitary napkin.

Additionally, one more advantage is that the present superabsorbent polymers have an ultimate free water absorption property (i.e., the total amount of water absorbed when the superabsorbent polymer is allowed to remain long enough, usually 3 to 5 minutes, in water until no more water can be absorbed) that is essentially similar to that of prior art superabsorbent polymers, and consequently, the present superabsorbent polymers are just as absorbent as those of the prior art.

Some of the objects and advantages of the invention having been stated, other objects and advantages will become evident as the description proceeds, when taken in connection with the Laboratory Examples described below.

DETAILED DESCRIPTION OF THE INVENTION

As long as the above-mentioned two-part thermal profile is performed on particulate superabsorbent polymer, the particulate superabsorbent polymer may be manufactured by any of the prior art processes for making superabsorbent polymers. For instance, the superabsorbent polymer may be made by the solvent polymerization technique or may be made by the inverse suspension or emulsion polymerization technique, which are well known techniques as discussed above.

Thus, the superabsorbent polymer may be obtained by polymerizing at least about 10%, more preferably about 25%, and even more preferably about 55 to about 99.9%, by weight of monomers having olefinically-unsaturated carboxylic and/or sulfonic acid groups. Such acid groups include, but are not limited to, acrylic acids, methacrylic acids, 2-acrylamido-2-methylpropane sulfonic acid, and mixtures thereof. The acid groups are present as salts, such as sodium, potassium, or ammonium salts.

The acid groups are typically neutralized to at least about 25 mol %. Preferably, the extent of neutralization is to at least about 50 mol %. More particularly, the preferred superabsorbent polymer has been formed from cross-linked acrylic acid or methacrylic acid, which has been neutralized to an extent of about 50 to about 80 mol %.

Additional useful monomers for making the superabsorbent polymers include from above 0 up to about 60% by weight of acrylamide, methacrylamide, maleic acid, maleic anhydride, esters (such as hydroxyethyl acrylate, hydroxyethylmethacrylate, hydroxypropylmethacrylate, glycidylmethacrylate, and dimethyl-aminoalkyl-methacrylate), dimethyl-aminopropyl acrylamide, and acrylamidopropyl trimethyl-ammonium chloride. Percentages below about 60% of these monomers are desirable as percentages above about 60% typically will have a detrimental effect and deteriorate the swell capacity of the resultant superabsorbent polymer.

Suitable network cross-linking agents useful in making the superabsorbent polymers are those which have at least two ethylenically unsaturated double bonds, those which have one ethylenically unsaturated double bond and one functional group reactive toward acid groups, and those which have several functional groups reactive toward acid groups. Suitable kinds of network cross-linking agents include, but are not limited to, acrylate and methacrylate of polyols (such as butanediol diacrylate, hexanediol dimethacrylate, polyglycol diacrylate, trimethylolpropane triacrylate, tetrahydrofurfuryl-2-methacrylate, glycerol dimethacrylate, allyloxy polyethylene glycol methacrylate, and ethoxylated trimethylolpropane triacrylate), allyl acrylate, diallyl acrylamide, triallyl amine, diallyl ether, methylenebisacrylamide, N,N-dimethylaminoethylmethacrylate, N-dimethylaminopropyl methacrylamide, N-methylol methacrylamide, and N-methylolacrylamide. These network cross-linking agents are distinguished from and not to be confused with the surface cross-linking agents discussed below.

Furthermore, depending on the desired end use, the superabsorbent polymer may have a water-soluble polymeric component. The content may range from above 0 up to about 30% by weight of a component that includes, but is not limited to, partially or completely saponified polyvinyl alcohol, polyvinyl pyrrolidone, starch, starch derivatives, polyglycols, polyacrylic acids, and combinations thereof. The molecular weight of the component is not critical, provided that it is water-soluble. Preferred water-soluble polymeric components are starch, polyvinyl alcohol, and mixtures thereof. Preferably, the content of the water-soluble polymeric component in the superabsorbent polymer ranges from about 1 to about 5% by weight, especially if starch and/or polyvinyl alcohol are present as the water-soluble polymeric component. Also, the water-soluble polymeric component may be present as a graft polymer having the acid-groups-containing polymer.

In connection with the particle shape of the superabsorbent polymer, there are no specific limitations. The superabsorbent polymer may be in the form of small spheres obtained by inverse suspension polymerization, or in the form of irregularly shaped particles obtained by drying and pulverizing the gel mass obtained by solvent polymerization. A typical particle size distribution ranges between about 20 and about 2000 micrometers, preferably between about 40 and about 890 micrometers, and more preferably between about 90 and about 850 micrometers.

As is well known, the smaller the particle size, then the faster a superabsorbent polymer will absorb water, and likewise, the larger the particle size, then the slower a superabsorbent polymer will absorb water. Hence, for the present invention, the particulate superabsorbent polymer desirably has the larger particle sizes, especially for use in making a core composite by the wet-laid process. Sizes under about 30 micrometers are generally unsuitable for the wet-laid process. Nevertheless, for any given particle size, the superabsorbent polymer of the present invention should absorb less water in a selected amount of seconds (i.e., exhibit a decreased, lower free water absorption) as compared to a prior art superabsorbent polymer of essentially the same particle size.

In general, the prior art processing technique for the manufacture of superabsorbent polymers ends with a heat treatment. This is not to be confused with the special two-part thermal profile that is critical in connection with manufacture of the superabsorbent polymers of the present invention so that they will have the desirably low free water absorption characteristics.

More specifically, the following is noted with respect to the two-part thermal profile required for the present invention. The heating of each of the two parts should be sufficient and the time of each of the two parts should be sufficient to achieve the inventive superabsorbent polymer with the desirable free water absorption property, as described below.

In the first part, after the polymeric particles have been ground and then sieved to the appropriate, desirable size, they are heated by being subjected to an increasing temperature. Typically, this is a temperature starting at about 50° C., more preferably about 55° C., and even more preferably about 60° C., and ending at about 170° C., more preferably about 190° C., and even more preferably about 220° C. Then, for the second part, the temperature is quickly brought to at least about 5° C. higher than the ending temperature of the first part, and maintained at that higher temperature. Preferably, the second part constant temperature is no more than about 50° C. higher, more preferably no more than about 30° C. higher, and even more preferably no more than about 10° C. higher than the first part ending temperature.

The heating and the time for each of part one and part two of the required two-part temperature profile should be sufficient so that the resultant superabsorbent polymeric particles exhibit a significantly reduced free water absorption, as compared to prior art superabsorbent polymeric particles of substantially the same particle size. In particular for the inventive particulate superabsorbent polymer, the slower free water absorption at about 6 seconds should be less than about 3 grams of water per gram of polymer, and in many instances, is less than about 2 grams of water per gram of superabsorbent polymer.

The free water absorption of the inventive superabsorbent polymer is referred to as delayed, reduced, or slower, as it is intended to mean the free water absorption in a short amount of time, i.e., 6 seconds. This is distinguished from free water absorption where the superabsorbent polymer is allowed to absorb water until no more water can be absorbed, which typically is 3 to 5 minutes, and is called the ultimate free water absorption as a reference to the total amount of water absorbed regardless of how long that takes. The inventive superabsorbent polymers have an ultimate free water absorption essentially the same as prior art superabsorbent polymers commercially used in sanitary articles.

A typical time for the first part of the temperature profile ranges from about 30 minutes to about 90 minutes, more preferably from about 45 minutes to about 75 minutes, even more preferably from about 55 minutes to about 65 minutes, and most preferably is about 60 minutes. Shorter times may be employed when higher temperatures are employed. The time for the second part of the required thermal profile is, in general, about the same as that for the first part, and likewise, shorter times may be employed with higher temperatures.

The superabsorbent polymers according to the present invention may be manufactured on a large scale by continuous or discontinuous processes.

Furthermore, the superabsorbent polymers according to the present invention may be used for a wide variety of applications, for instance, sanitary articles, water-blocking tapes and sheets for wherever leaking water is a problem (i.e., inside of fiber-optic communication cables and power transmission cables, between concrete blocks that make up the walls of an underwater tunnel, such as the Channel Tunnel connecting England and France, as mentioned in the above-noted Buchholz journal article), and carriers for insecticides, pesticides and/or herbicides.

When the inventive superabsorbent polymers are used to make a web that will be employed as a core composite in a sanitary article, the weight ratio of polymer component to fibrous component in the web should be controlled to range from about 90:10 to about 5:95. A very suitable web has a ratio from about 35:65 to about 45:55, and more preferably has a ratio of about 40:60.

Although comminuted wood pulp (i.e., cellulosic fibers, colloquially referred to as fluff) is preferred to form the fibrous component of the web for this invention, other wettable fibers such as cotton linters can be used. Additionally, the fibrous component may be formed from meltblown synthetic fibers such as polyethylene, polypropylene, polyesters, copolymers of polyesters and polyamides, and the like. The fibrous component may also be formed from a mixture of wood pulp fluff and one or more of the meltblown fibers. For example, the fibrous component may comprise at least about 5 weight % preferably about 10 weight % synthetic polymer fibers and the remainder may comprise wood pulp fluff. The fibers of the web are generally hydrophilic or rendered hydrophilic through a surface treatment. Cellulosic fiber is preferred, a preferred one being sold under the trademark GOLDEN ISLES® by Georgia Pacific.

Especially, the inventive superabsorbent polymers, due to their free water absorption characteristics, are very useful in a wet-laid process for manufacturing a wet-laid web, having a superabsorbent polymer component mixed with a fibrous component and useful as a core composite in a sanitary article. Examples of the wet-laid process are described in the above-mentioned published European Patent Application No. 0 437 816 A1 and U.S. Pat. No. 4,605,401. As the wet-laid process involves mixing an aqueous slurry of superabsorbent polymer with fiber, water is absorbed during the wet-laid process. Consequently, at the end of the wet-laid process, the wet-laid web must be dried prior to placing it as a core composite in an end use article, such as a disposable diaper.

By employing the superabsorbent polymers of the present invention, less water should be absorbed during the wet-laid process of making a web. Thus, there should be less water to remove during drying, resulting in a shorter drying time for the wet web, which is very advantageous in a large scale factory production setting.

Moreover, after drying of the wet-laid web, due to the free water absorbency characteristics of the superabsorbent polymer, the web will have an improved solids content, as compared to a wet-laid web containing prior art superabsorbent polymer. Typically, the inventive wet-laid web will have a solids content above about 18%.

Furthermore, the inventive superabsorbent polymers are well suited for use in a web, since they typically exhibit an acceptable centrifuge retention capacity like that exhibited by prior art superabsorbent polymers. The inventive superabsorbent polymers usually display a centrifuge retention capacity of more than about 28, often more than about 30, and even more than about 32 grams of aqueous saline per gram of superabsorbent polymer.

Additionally, the inventive superabsorbent polymers are well suited for use in a web, since they typically exhibit an acceptable absorbency under load property, like that exhibited by prior art superabsorbent polymers. The inventive superabsorbent polymers usually display an absorbency under load property of more than about 13, often more than about 15, and even more than about 18 grams of aqueous saline per gram of superabsorbent polymer.

As is known from the above-mentioned U.S. Pat. No. 5,409,771, coating a particulate superabsorbent polymer with an alkylene carbonate followed by heating to effect surface cross-linking improves the absorbency under load characteristics. A desirable absorbency under load property of at least about 13 grams of aqueous saline per gram of superabsorbent polymer is especially desirable when the end use of the superabsorbent polymer is in a sanitary article, such as a disposable diaper, that is subjected to pressure from the person wearing the article.

Thus, the superabsorbent polymers of the present invention are preferably coated with a surface X-linking agent prior to the inventive two-part thermal profile. The preferred alkylene carbonate for surface cross-linking is ethylene carbonate.

More specifically, as described in U.S. Pat. No. 5,409,771, for coating of particulate superabsorbent polymer with a surface X-linking agent, the polymer may be mixed with an aqueous-alcoholic solution of the alkylene carbonate surface X-linking agent. The amount of alcohol is determined by the solubility of the alkylene carbonate and is kept as low as possible for technical reasons, for instance, protection against explosions. Suitable alcohols are methanol, ethanol, butanol, or butyl glycol, as well as mixtures of these alcohols. The preferred solvent is water which typically is used in an amount of 0.3 to 5.0% by weight, relative to particulate superabsorbent polymer. In some instances, the alkylene carbonate surface X-linking agent is dissolved in water, without any alcohol. It is also possible to apply the alkylene carbonate surface X-linking agent from a powder mixture, for example, with an inorganic carrier material, such as $SiO_2$.

To achieve the desired surface X-linking properties, the alkylene carbonate has to be distributed evenly on the particulate superabsorbent polymer. For this purpose, mixing is effected in suitable mixers, such as fluidized bed mixers, paddle mixers, milling rolls, or twin-worm-mixers. It is also possible to carry out the coating of the particulate superabsorbent polymer during one of the process steps in the production of the particulate superabsorbent polymer. A particularly suitable process for this purpose is the inverse suspension polymerization process.

According to U.S. Pat. No. 5,409,771, the thermal treatment which follows the coating treatment is carried out as follows. In general, the thermal treatment is at a temperature between 150 and 300° C. However, if the preferred alkylene carbonates are used, then the thermal treatment is at a temperature between 180 and 250° C. The treatment temperature depends on the dwell time and the kind of alkylene carbonate. At a temperature of 150° C., the thermal treatment is carried out for several hours. On the other hand, at a temperature of 250° C., a few minutes, e.g., 0.5 to 5 minutes, are sufficient to achieve the desired surface X-linking properties. The thermal treatment may be carried out in conventional dryers or ovens. Examples of dryers and ovens include rotary kilns, fluidized bed dryers, disk dryers, or infrared dryers.

In contrast to the thermal treatment in U.S. Pat. No. 5,409,771, the present inventive thermal treatment (whether performed without or with the presence of a surface X-linking agent) comprises the above-described special two-part thermal profile. During the first part, the temperature is increased, and during the second part, the temperature is maintained at a constant temperature at least about 5° C. higher, preferably no more than about 50° C. higher, than the end temperature of the first part.

To characterize the superabsorbent polymers as set out in the Laboratory Examples below (both those superabsorbent polymers of the present invention, as well as those comparison, superabsorbent polymers), the centrifuge retention capacity (CRC), the absorbency under load (AUL), and the free water absorption (FWA) were measured in the following manner.

CRC. The SAP's retention was determined according to the tea bag test method and reported as an average value of two measurements. Approximately 200 mg of SAP, that have been sieved to a particle size distribution of 300 to 600 micrometers (not the indicated particle sizes in the Examples below), were enclosed in a tea bag and immersed in 0.9% by weight aqueous NaCl solution for 30 minutes. Then, the tea bag was centrifuged at 1600 rpm for 3 minutes (centrifuge diameter was about 18 cm) and weighed. Two tea bags without SAP were used as blanks.

Then, the CRC was calculated according to the following equation.

$$CRC = \frac{W_3 - W_2 - W_1}{W_1}$$

where:
CRC=Retention after an immersion time of 30 minutes (g of liquid absorbed/g of SAP)
$W_1$=Initial Weight of SAP (g)
$W_2$=Weight of the average blank tea bags (without SAP) after centrifugation (g)
$W_3$=Weight of the tea bag with SAP after centrifugation (g)

AUL. The SAP's absorbency of a 0.9% by weight aqueous NaCl solution under load was determined according to the method described on page 7 of the above-mentioned published European Patent Application No. 0 339 461 A1. An initial weight of the SAP was placed in cylinder with a sieve bottom. The SAP was loaded by a piston exerting a pressure load of 60 g/cm$^2$. (It is noted 60 g/cm$^2 \approx$ 0.9 psi.)

The cylinder was subsequently placed on a Demand-Absorbency-Tester (DAT) on a glass fritted disk of 125 mm diameter, and covered by a Whatman filter paper #3. Then, the SAP was allowed to absorb the 0.9% NaCl solution for 1 hour. The initial weight of the SAP was approximately 160 mg, which had been sieved to a particle size distribution of 300 to 600 micrometers (not the indicated particle sizes in the Laboratory Examples below).

After the 1 hour, the swollen SAP was re-weighed, and grams of the 0.9% NaCl solution that had been retained was calculated. The AUL of the SAP was the grams retained.

FWA. To determine the SAP's free water absorption, a vacuum apparatus was assembled. More specifically, a vacuum pump was attached, by Tygon tubing, to a vacuum flask, atop which was positioned the bottom portion of a Buchner funnel, that was sealed properly to the flask using a one-hole rubber stopper. A magnetic stirrer was placed beside the apparatus. After assemblage of the apparatus, the vacuum pump was engaged and allowed to stay on throughout all FWA testing.

Using a 250 ml graduated cylinder, 150 ml±1 ml of 23.0° C.±0.5° tap H$_2$O was measured into a 250 ml beaker containing a 1 inch stir bar. The beaker of H$_2$O was placed on a stir plate and allowed to stir so that the created vortex ended approximately 2 to 3 cm from the surface of the liquid.

A dry, 80 mesh (180 micrometer) sieve was tared on a top loading balance, and then placed atop the Buchner funnel and tightly anchored through suction. The SAP was then weighed on a separate balance in the amount needed for the particular test: the 30 second FWA determination employed 1 gram of SAP, while the 15 second and the 6 second determinations each employed 3 grams of SAP. The SAP was poured into the beaker of H$_2$O, while simultaneously a stopwatch was started to count time from 0. When the SAP was poured into the tap H$_2$O, dispersion of the discrete particles was immediate and complete in that no discrete particles tended to clump or aggregate.

Upon reaching the number of seconds desired, the beaker contents were poured into a sieve, with a transfer time of no greater than 3 additional seconds. The sieve was left under the vacuum for approximately 30 additional seconds. The sieve was then removed from the Buchner funnel, and wiped on its bottom surface of mesh to remove any residual H$_2$O. The dried sieve was then placed onto a previously tared balance and the "Gel Weight" recorded.

Then, the FWA (g of liquid absorbed/g of SAP) was calculated from the gel weight according to the following equation.

$$FWA(g/g) = \frac{g \text{ Gel Weight} - g \text{ Superabsorbent}}{g \text{ Superabsorbent}}$$

LABORATORY EXAMPLES

I. Comparison Examples (of Commercially Available SAPs)

EXAMPLE A

Various commercially available, prior art superabsorbent polymers were tested for FWA, CRC, and AUL. For the FWA test, each of the prior art superabsorbent polymers was tested at 27° C. at 750 rpm agitation speed, and had a full particle size distribution of 44 to 841 micrometers. For the CRC test and the AUL test, each of the prior art superabsorbent polymers was sieved so that tested was the above-noted particle size distribution of 300 to 600 micrometers. The FWA test was conducted with water, whereas each of the CRC test and the AUL test was conducted with 0.9% by weight aqueous saline. The results are summarized below in Table IA.

TABLE IA

| Prior Art SAP and Supplier Company | 6 seconds FWA (g/g) | 15 seconds FWA (g/g) | 30 seconds FWA (g/g) | CRC (g/g) | AUL (g/g) |
|---|---|---|---|---|---|
| IM-4510 from Hoechst Celanese | 23.7 | 31.7 | 59.1 | 32.6 | 21.0 |
| ASAP-2300 from Chemdal | 7.6 | 12.3 | 31.7 | 32.2 | 21.5 |
| Sumitomo-60S from Sumitomo | 10.8 | 20.8 | 50.9 | 36.9 | 9.6 |
| SalSorb-CL20 from Allied Chemical | 8.9 | 14.8 | 23.1 | 36.5 | 11.9 |
| FAVOR ® SXM-77 from Stockhausen | 5.6 | 11.5 | 18.7 | 36.5 | 21.0 |

As can be seen, each prior art superabsorbent polymer exhibited a FWA at 6 seconds greater than 5 g/g.

EXAMPLE B

Next, various selected particle size distributions of Stockhausen's FAVOR® SXM-77 were tested for FWA at 23° C.

at 750 rpm agitation speed. The results are summarized below in Table IB.

TABLE IB

| Particle Size (in micrometers) | Particle Size (in U.S. standard meshes) | 15 seconds FWA (g/g) |
|---|---|---|
| 44 to 841 | −20/+325 | 10.9 |
| 595 to 841 | −20/+30 | 5.5 |
| 420 to 595 | −30/+40 | 7.3 |
| 297 to 420 | −40/+50 | 12.6 |
| 149 to 297 | −50/+100 | 26.1 |
| 88 to 149 | −100/+170 | 53.6 |
| 44 to 88 | −170/+325 | 73.3 |

As can be seen, only the largest particle size distribution (595 to 841 micrometers) of superabsorbent SXM-77 exhibited a slow and low FWA at 15 seconds of 5.5 g/g, which is in keeping with, as noted above, the inverse relationship that as the particle size increased, then the FWA decreased.

In contrast, as discussed in more detail below in Laboratory Examples II A through H vis-a-vis superabsorbent polymers according to the present invention, the full particle size distribution of 90 to 850 micrometers for these superabsorbent polymers typically exhibited a FWA at 15 seconds of 4.0 g/g or less, and only one sample of this full particle size distribution exhibited a FWA at 15 seconds of 6.4 g/g.
II. Examples A through H (of SAPs of Present Invention) and Comparison Examples A and B (of SAPs without Treatment of Two-Part Thermal Profile)

In the following examples, each superabsorbent polymer was a cross-linked sodium polyacrylate made by solvent polymerization. Also, each percentage recited was a weight %, unless specifically indicated otherwise as a mol %, and the aqueous ethylene carbonate was a solution of 50 parts by weight of ethylene carbonate and 50 parts by weight of deionized water.

EXAMPLE A

An aqueous acrylic acid solution comprising 0.1% EO-TMPTA as a cross-linking agent, 0.25% AII-PEGMA as a co-cross-linking agent, and 2.5% methoxy polyethylene glycol methacrylate, all relative to acrylic acid, was neutralized with sodium hydroxide solution under cooling. The acrylic acid concentration of the monomer solution amounted to 29%, with a neutralization degree of 70 mol %.

The monomer solution was cooled to about 5° C., purged with nitrogen, and then mixed with sodium erythobate solution as a reducing agent, hydrogen peroxide solution as an oxidant, (the sodium erythobate forming a redox initiator couple with the hydrogen peroxide), sodium carbonate solution as a foaming agent to generate a porous polymer gel, and a fourth solution containing both ABAH and sodium persulfate as thermal initiators which generate free radicals throughout the course of the reaction to complete the polymerization. The final concentration of each of sodium erythobate, hydrogen peroxide, sodium carbonate, ABAH, and sodium persulfate was respectively at 57, 125, 600, 125, and 100 ppm, all relative to total monomer solution.

Polymerization started immediately after the monomer solution was mixed with all other solutions. After 20 minutes of polymerization, the formed polymer gel was crumbled and dried in hot air at 150° C. for 20 minutes.

The dried polymer was subsequently ground, screened to 90 to 850 micrometers and continuously fed into a paddle mixer (380 rpm) at 4000 kg/hour while mixing with aqueous ethylene carbonate at a 1:167 ratio by weight of ethylene carbonate to polymer in order to coat this surface cross-linking agent onto the polymer.

The mixture was then transferred to a conveyor where it was heated from a beginning temperature of 65° C. to a final temperature of 185° C. within 1 hour for the first part of the thermal profile. Subsequently, the mixture was rapidly brought to 200° C. and maintained at that constant temperature of 200° C. for an additional 45 minutes for the second part of the thermal profile. After cooling, the resultant product was transported to a storage vessel.

EXAMPLE B

The same procedure as described in Example A was used except that for the second part of the thermal profile, the mixture was maintained for 35 minutes at a constant temperature of 210° C. after the polymer/ethylene carbonate mixture had been heated for the first part of the thermal profile to a final temperature of 185° C. The resultant product was transported to a storage vessel after cooling.

EXAMPLE C

The same procedure as described in Example A was used except that for the second part of the thermal profile, the mixture was maintained for 50 minutes at a constant temperature of 205° C. after the polymer/ethylene carbonate mixture had been heated for the first part of the thermal profile to a final temperature of 185° C. The resultant product was transported to a storage vessel after cooling.

EXAMPLE D

An aqueous acrylic acid solution comprising 0.19% triallyl amine as a cross-linking agent, relative to acrylic acid, was neutralized with sodium hydroxide solution under cooling. The acrylic acid concentration of the monomer solution amounted to 31%, with a neutralization degree of 70 mol %.

The monomer solution was cooled to about 5° C., purged with nitrogen, and then mixed with sodium erythobate solution as a reducing agent, t-butyl hydrogen peroxide solution as an oxidant, (the sodium erythobate forming a redox initiator couple with the t-butyl hydrogen peroxide), and a third solution containing both ABAH and sodium persulfate as thermal initiators which generate free radicals throughout the course of the reaction to complete the polymerization. The final concentration of each of sodium erythobate, t-butyl hydrogen peroxide, ABAH, and sodium persulfate was respectively at 26, 182, 195, and 100 ppm, all relative to total monomer solution.

Polymerization started immediately after the monomer solution was mixed with all other solutions. After 20 minutes of polymerization, the formed polymer gel was crumbled and dried in hot air at 150° C. for 20 minutes.

The dried polymer was subsequently ground, screened to 90 to 850 micrometers and continuously fed into a paddle mixer (380 rpm) at 4000 kg/hour while mixing with aqueous ethylene carbonate as a surface cross-linking agent at a 1:167 ratio by weight of ethylene carbonate to polymer in order to coat this surface cross-linking agent onto the polymer.

The mixture was then transferred to a conveyor where it was heated from a beginning temperature of 80° C. to a final temperature of 170° C. within 1 hour for the first part of the thermal profile. Subsequently, the mixture was maintained at a constant temperature of 200° C. for an additional 60 minutes for the second part of the thermal profile. After cooling, the resultant product was transported to a storage vessel.

EXAMPLE E

The same procedure as described in Example D was used except that for the second part of the thermal profile, the mixture was maintained for an additional 60 minutes at a constant temperature of 205° C., after the polymer/ethylene carbonate mixture had been heated to the final temperature of 170° C. for the first part of the thermal profile. The resultant product was transported to a storage vessel.

EXAMPLE F

The same procedure as described in Example D was used except that for the second part of the thermal profile, the mixture was maintained for an additional 45 minutes at a constant temperature of 210° C. after the polymer/ethylene carbonate mixture had been heated to the final temperature of 170° C. for the first part of the thermal profile. The resultant product was transported to a storage vessel after cooling.

EXAMPLE G

An aqueous acrylic acid solution comprising 0.19% tri-allyl amine as a cross-linking agent, relative to acrylic acid, was neutralized with sodium hydroxide solution under cooling. The acrylic acid concentration of the monomer solution amounted to 31%, with a neutralization degree of 60 mol %.

The monomer solution was cooled to about 5° C., purged with nitrogen, and then mixed with ascorbic acid solution as a reducing agent, t-butyl hydrogen peroxide solution as an oxidant, (the ascorbic acid forming a redox initiator couple with the t-butyl hydrogen peroxide), and a third solution containing both ABAH and sodium persulfate. The final concentration of each of ascorbic acid, t-butyl hydrogen peroxide, ABAH, and sodium persulfate was respectively at 22, 178, 200, and 100 ppm, all relative to total monomer solution.

Polymerization started immediately after the monomer solution was mixed with all other solutions. After 20 minutes of polymerization, the formed polymer gel was crumbled and dried in hot air at 150° C. for 20 minutes.

The dried polymer was subsequently ground, screened to 90 to 850 micrometers and continuously fed into a paddle mixer (380 rpm) at 4000 kg/hour while mixing with aqueous ethylene carbonate as a surface cross-linking agent, at a 1:206 ratio by weight of ethylene carbonate to polymer in order to coat this surface cross-linking agent onto the polymer.

The mixture was then transferred to a conveyor where it was heated from a beginning temperature of 80° C. to a final temperature of 175° C. within 1 hour for the first part of the thermal profile. Subsequently, the mixture was maintained at a constant temperature of 180° C. for an additional 45 minutes for the second part of the thermal profile. After cooling, the resultant product was transported to a storage vessel.

EXAMPLE H

The same procedure as describe in Example G was used except that for the second part of the thermal profile, the mixture was maintained for an additional 35 minutes at a constant temperature of 190° C. after the polymer/ethylene carbonate mixture had been heated to the final temperature of 175° C. The resultant product was transported to a storage vessel after cooling.

Comparison Example A (With Only First Part of Two-part Thermal Profile)

The polymer prepared as described in Example E was dried, ground, screened to 90 to 850 micrometers, and continuously fed into a paddle mixer (380 rpm) at 4000 kg/hour while mixing with ethylene carbonate as a surface cross-linking agent at a 1:167 ratio by weight of ethylene carbonate to polymer in order to coat this surface cross-linking agent onto the polymer.

The mixture was then transferred to a conveyor where it was heated from a beginning temperature of 80° C. to a final temperature of 175° C. within 1 hour as the first part of the thermal profile, and then after cooling, the resultant product was transferred to a storage vessel. The second part of the thermal profile was not performed.

Comparison Example B (With Only Second Part of Two-part Thermal Profile)

The polymer prepared as described in Example E was dried, ground, screened to 90 to 850 micrometers, and continuously fed into a paddle mixer (380 rpm) at 4000 kg/hour while mixing with ethylene carbonate at a 1:167 ratio by weight of ethylene carbonate to polymer in order to coat this surface cross-linking agent onto the polymer.

The mixture was then transferred to a conveyor where it was heated at a constant temperature of 205° C. for 2 hours for the second part of the thermal profile. The resultant product was cooled and transported to a storage vessel. The first part of the thermal profile was not performed.

The resultant superabsorbent polymers of Examples A through H and Comparison Examples A and B were tested for FWA, CRC, and AUL. For the FWA test, the particle size distribution was the full 90 to 850 micrometers. However, for the CRC test and the AUL test, the polymers were sieved, and hence, the particle size distribution was the above-noted 300 to 600 micrometers. The FWA test was conducted with water, whereas each of the CRC test and the AUL test was conducted with 9% by weight aqueous saline. The results are summarized below in Table II.

TABLE II

| Example of SAP | 6 seconds FWA (g/g) | 15 seconds FWA (g/g) | 30 seconds FWA (g/g) | CRC (g/g) | AUL (g/g) |
| --- | --- | --- | --- | --- | --- |
| Ex. A | 2.6 | 6.4 | 18.8 | 33.5 | 19.2 |
| Ex. B | 1.9 | 4.0 | 14.0 | 30.3 | 21.6 |
| Ex. C | 1.3 | 3.0 | 11.3 | 28.4 | 19.7 |
| Ex. D | 0.9 | 2.8 | 10.0 | 33.0 | 15.6 |
| Ex. E | 1.1 | 2.4 | 9.3 | 35.3 | 13.7 |
| Ex. F | 1.2 | 2.7 | 8.3 | 31.9 | 14.7 |
| Ex. G | 1.5 | 3.3 | 9.7 | 30.0 | 18.2 |
| Ex. H | 1.6 | 3.6 | 10.2 | 29.4 | 20.3 |
| Comparison A | 5.7 | 13.5 | 22.4 | 38.3 | 11.5 |
| Comparison B | 3.8 | 11.4 | 35.2 | 37.9 | 10.0 |

As can be seen, for the inventive superabsorbent polymers that had been subjected to the two-part thermal profile, each exhibited a FWA at 6 seconds less than 3 g/g, and most exhibited a FWA at 6 seconds less than 2 g/g. On the other hand, for the two comparisons that had been subjected to only one of the two parts of the thermal profile, each exhibited a FWA at 6 seconds greater than 3.5 g/g. Moreover, each of the superabsorbent polymers that had been subjected to the two-part thermal profile exhibited a far superior AUL, as compared to the AUL of each of the two comparisons.

III. Examples of Web of SAP and Cellulosic Fluff made by Wet-Laid Process

In the following examples, selected inventive SAPs and also the two comparison SAPs, made as described above in Example II, were each respectively employed in a wet-laid process to make a wet-laid web of SAP and cellulosic fiber.

More specifically, 1.36 grams of cellulosic fiber (GOLDEN ISLES®4800 sold by Georgia Pacific) was added to 200 grams of tap water, and then, 0.9 gram of the selected SAP was added. The resultant slurry was then poured into a laboratory web molder having a 150 micrometer polyester screen at the bottom.

The web molder was made with a stainless steel, sampling chamber on the top for retaining the slurry. The chamber measured 8.5 cm in diameter and 10 cm in height. Also, the web molder had a bottom section that was connected through a ball valve to a vacuum system.

The slurry was agitated with a 3-blade fan-shaped turbine agitator moving in an up-and-down fashion for 5 times. The water temperature was controlled at 23° C.±1° C., and the total water contact time of the SAP and cellulosic fiber mixture was controlled to be 10 seconds. Next, the water was drained under vacuum (60 mm Hg) from the slurry, with a draining time of 60 seconds.

The solids content of each respective web was determined according to the following equation:

Solids wt %=[(fiber wt+SAP wt)/web wt]×100% where each wt (i.e., the weight of fiber, the weight of SAP, and the weight of web) was in grams. The results are summarized below in Table III.

TABLE III

| Example of SAP | SAP/Cellulosic Fiber Ratio (weight/weight) | Web Solids Content (weight %) |
| --- | --- | --- |
| none | 0/100 | 23.9 |
| Example A | 40/60 | 18.1 |
| Example C | 40/60 | 21.6 |
| Example D | 40/60 | 22.1 |
| Example E | 40/60 | 23.9 |
| Example F | 40/60 | 23.0 |
| Example H | 40/60 | 22.1 |
| Comparison A | 40/60 | 16.3 |
| Comparison B | 40/60 | 17.7 |

As can be seen from the above Table III, wet-laid webs made with the inventive SAPs (Examples A, C, D, E, F, and H) exhibited an improved solids content versus wet-laid webs made with the comparison SAPs (Comparison Examples A and B). More specifically, the solids content for each of the wet-laid webs made with the inventive SAPs was always above 18%, whereas the solids content for each of the wet-laid webs made with the comparison SAPs was always below 18%.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method for making a delayed absorption, particulate superabsorbent polymer, said method comprising:

(a) preparing a particulate superabsorbent polymer, and (b) subjecting the particulate superabsorbent of step (a) to a thermal profile having a first part and a second part, wherein the first part comprises heating the superabsorbent polymer with an increasing temperature from a beginning temperature to a final increased temperature and the second part comprises maintaining heating of the superabsorbent polymer at a constant temperature that is at least about 5° C. higher than the final increased temperature of the first part, and wherein the temperatures and the times for heating of each of the first part and the second part are sufficient to achieve a delayed absorption, particulate superabsorbent polymer having a free water absorption property of absorbing less than about 3 grams of aqueous saline per gram of superabsorbent polymer in about 6 seconds, for a full particle size distribution ranging from about 40 micrometers to about 890 micrometers.

2. The method of claim 1, wherein the constant temperature for maintaining the heating in the second part is a constant temperature from about 5° C. to about 50° C. higher than the final increased temperature of the first part.

3. The method of claim 1, wherein the temperature of the first part increases from a beginning temperature between about 50° C. and about 80° C. to a final increased temperature between about 170° C. and about 220° C., and the constant temperature in the second part is between about 175° C. and about 270°.

4. The method of claim 1, wherein the time for the heating of the first part ranges from about 30 minutes to about 90 minutes.

5. The method of claim 1, wherein the time for the heating of the second part ranges from about 30 minutes to about 90 minutes.

6. The method of claim 1, wherein the superabsorbent polymer has a free water absorption property of absorbing less than about 6 grams of water per gram of superabsorbent polymer in about 15 seconds, for a full particle size distribution ranging from about 40 micrometers to about 890 micrometers.

7. The method of claim 1, wherein the superabsorbent polymer has a centrifuge retention capacity property of retaining more than 28 grams of aqueous saline per gram of superabsorbent polymer.

8. The method of claim 1, wherein the superabsorbent polymer has an absorbency under load property of retaining more than 13 grams of aqueous saline per gram of superabsorbent polymer.

9. The method of claim 1, wherein step (a) includes a coating treatment with a surface cross-linking agent and step (b) is performed after the coating treatment.

* * * * *